US007639355B2

(12) United States Patent
Fattal et al.

(10) Patent No.: US 7,639,355 B2
(45) Date of Patent: Dec. 29, 2009

(54) ELECTRIC-FIELD-ENHANCEMENT STRUCTURE AND DETECTION APPARATUS USING SAME

(75) Inventors: David A. Fattal, Mountain View, CA (US); Zhiyong Li, Redwood City, CA (US); William M. Tong, San Francisco, CA (US); Duncan Stewart, Menlo Park, CA (US); Jason Blackstock, Cambridge, MA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 11/823,281

(22) Filed: Jun. 26, 2007

(65) Prior Publication Data
US 2009/0002701 A1    Jan. 1, 2009

(51) Int. Cl.
*G01J 3/44* (2006.01)
(52) U.S. Cl. .................................. 356/301; 356/445
(58) Field of Classification Search .............. 356/301, 356/445, 300
See application file for complete search history.

(56) References Cited

U.S. PATENT DOCUMENTS

| 5,067,788 | A | 11/1991 | Jannson |
| 6,198,869 | B1* | 3/2001 | Kraus et al. ................. 385/129 |
| 2003/0206708 | A1 | 11/2003 | Estes |
| 2006/0034729 | A1* | 2/2006 | Poponin ................... 422/82.05 |
| 2007/0134902 | A1* | 6/2007 | Bertino et al. .............. 438/610 |

OTHER PUBLICATIONS

International Search Report; PCT Patent Application No. PCT/US2008/007934, filed Jun. 25, 2008; search issued by Korean Patent Office (ISA) Dec. 31, 2008.

* cited by examiner

*Primary Examiner*—Gregory J Toatley, Jr.
*Assistant Examiner*—Abdullahi Nur (57) ABSTRACT

Various aspects of the present invention are directed to electric-field-enhancement structures and detection apparatuses that employ such electric-field-enhancement structures. In one aspect of the present invention, an electric-field-enhancement structure includes a substrate having a surface. The substrate is capable of supporting a planar mode having a planar-mode frequency. A plurality of nanofeatures is associated with the surface, and each of nanofeatures exhibits a localized-surface-plasmon mode having a localized-surface-plasmon frequency approximately equal to the planar-mode frequency.

20 Claims, 8 Drawing Sheets

ELECTRIC-FIELD-ENHANCEMENT STRUCTURE AND DETECTION APPARATUS USING SAME

TECHNICAL FIELD

Embodiments of the present invention are related generally to electric-field-enhancement structures for use in a number of different applications, such as detection apparatuses.

BACKGROUND

Enhancement of electric fields around metal particles is a topic of current scientific and technological interest. For example, surface enhanced Raman spectroscopy ("SERS") is a well-known spectroscopy technique that utilizes an enhanced electric field near a specially prepared, roughened metal surface or metal particles to increase the amount of inelastically scattered Raman radiation from an analyte. In SERS, the analyte is adsorbed onto or placed adjacent to an activated metal surface or structure. Irradiation of the analyte and the metal surface or particles with electromagnetic radiation ("EMR") of a selected frequency excites surface plasmon polaritons ("SPPs") in the metal surface or particles.

During SERS, the analyte experiences the intense, localized electric field of the SPP, and Raman photons characteristic of the analyte are inelastically scattered from the analyte. The enhanced electric field is considered one significant factor for the relatively increased Raman radiation compared to when Raman spectroscopy is practiced without the metal surface or particles. For example, the enhanced electric field from the metal surface may enhance the Raman scattering intensity by factors of between $10^3$ and $10^6$.

Recently, Raman spectroscopy has been performed employing randomly oriented metal nanoparticles, such as nanometer scale needles, islands, and wires, as opposed to a simple roughened metal surface, for enhancing electric fields. The intensity of the Raman scattered photons from a molecule adsorbed on such a metal surface may be increased by a factor greater than $10^6$. At this level of sensitivity, Raman spectroscopy can be used to detect minute amounts of species and is referred to as nano-enhanced Raman spectroscopy ("NERS").

As can be appreciated from the discussion above about SERS and NERS, enhancement of electric fields around metal particles can be of significant utility. In addition to SERS and NERS, enhancement of electric fields can be used in other applications, such as infrared spectroscopy, sensors, Raman imaging systems, nanoantennas, and many other applications. Accordingly, researchers and developers of electric-field-enhancement structures can appreciate a need for improved electric-field-enhancement structures that may be used in a wide variety of applications, such as sensors, Raman spectroscopy systems, and many other applications.

SUMMARY

Various aspects of the present invention are directed to electric-field-enhancement structures and detection apparatuses that employ such electric-field-enhancement structures. In one aspect of the present invention, an electric-field-enhancement structure includes a substrate having a surface. The substrate is capable of supporting a planar mode having a planar-mode frequency. A plurality of nanofeatures is associated with the surface, and each of the nanofeatures exhibits a localized-surface-plasmon mode having a localized-surface-plasmon frequency approximately equal to the planar-mode frequency. When excited by excitation electromagnetic radiation, the localized-surface-plasmon modes of the nanofeatures and the planar mode constructively interfere with each other to result in an enhanced electric field.

BRIEF DESCRIPTION OF THE DRAWINGS

The drawings illustrate various embodiments of the present invention, wherein like reference numerals refer to like elements or features in different views or embodiments shown in the drawings.

DETAILED DESCRIPTION OF VARIOUS EMBODIMENTS

Various embodiments of the present invention are directed to electric-field-enhancement structures and detection apparatuses that utilize such electric-field-enhancement structures. The disclosed embodiments for electric-field-enhancement structures include a plurality of nanofeatures associated with a surface of a substrate. A localized surface plasmon ("LSP") mode of each of the nanofeatures and a planar mode of the substrate may be excited responsive to EMR at a selected frequency to generate an enhanced electric field adjacent to the surface. The enhanced electric field may be used, for example, in SERS, infrared spectroscopy, and many other applications.

Figure 1A:
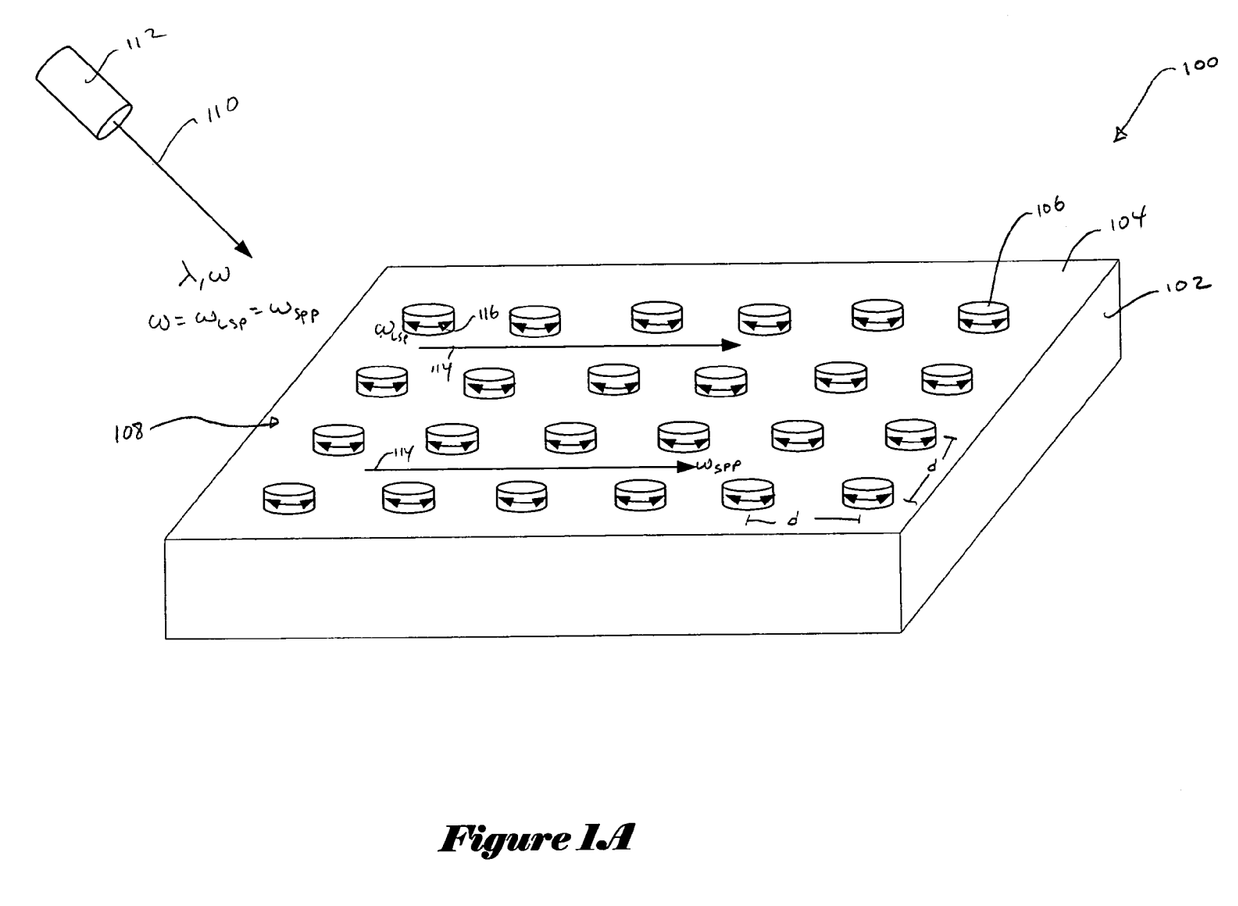
FIG. 1A is a schematic isometric view of an electric-field-enhancement structure according to one embodiment of the present invention.
Figure 1B:
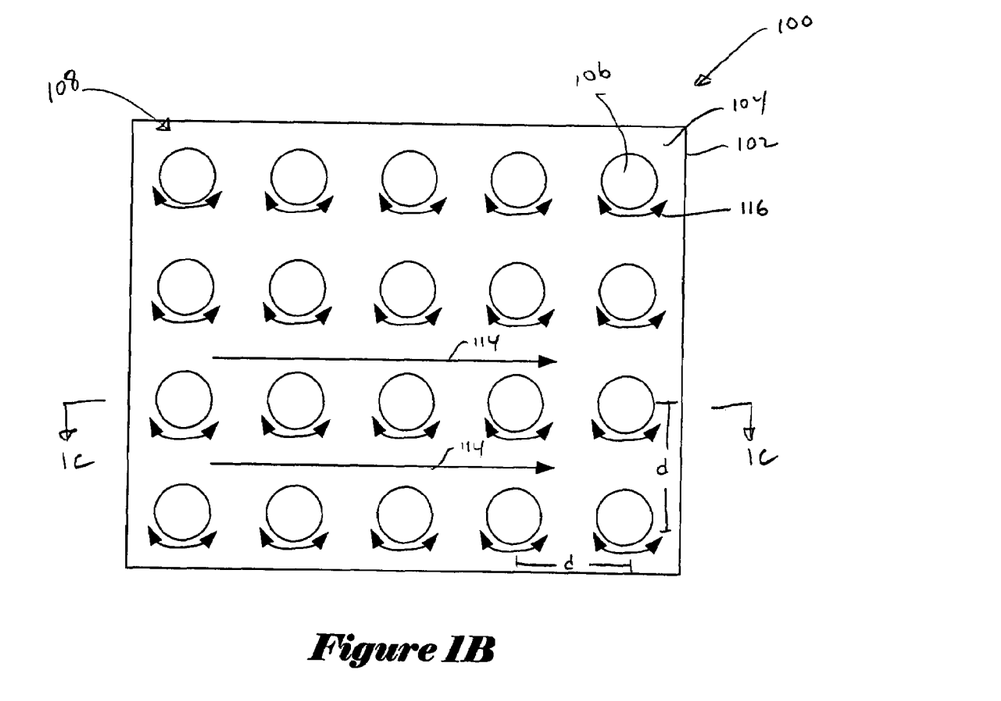
FIG. 1B is a schematic plan view of the electric-field-enhancement structure shown in FIG. 1A.
Figure 1C:
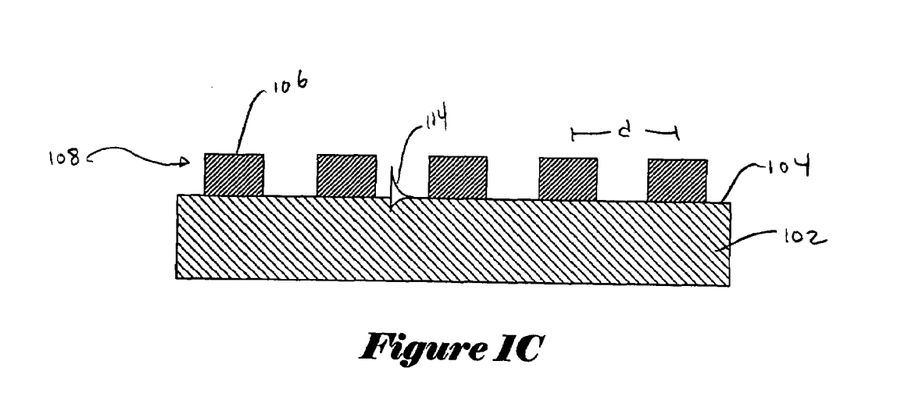
FIG. 1C is a schematic cross-sectional view of the electric-field-enhancement structure shown in FIG. 1B taken along line 1C-1C.

FIGS. 1A-1C show an electric-field-enhancement structure 100 according to one embodiment of the present invention. The electric-field-enhancement structure 100 includes a substrate 102 having a surface 104. A plurality of nanofeatures, such as nanoparticles 106, may be formed on the surface 104. Representative sizes for each of the nanoparticles 106 may be about 2 nm to about 200 nm. Additionally, the geometry of the nanoparticles 106 may depart from the illustrated geometry. For example, each of the nanoparticles 106 may be generally spherical, hemispherical, cylindrical, or another suitable geometry. As used herein, the term "nanofeature" refers to a nanoparticle or a nanohole. The nanoparticles 106 are distributed in a periodic arrangement on the surface 104 to form a diffraction grating 108. For example, the nanoparticles 106 are shown arranged in a square-lattice arrangement with a lattice parameter d. However, the plurality of nanoparticles 106 may exhibit other periodic arrangements, without limitation. A representative range for the distance d may be about 50 nm to several micrometers.

Each of the nanoparticles 106 is formed from a plasmon-active material, such as a metal, alloy, or degenerately-doped semiconductor material capable of having surface plasmons excited therein. For example, each of the nanoparticles 106 may be formed from copper, gold, palladium, silver, alloys of any of the preceding metals, or another suitable plasmon-active material. LSPs may be excited in each of the nanoparticles 106 responsive to excitation EMR at a specific frequency. Surface plasmons are oscillations of a free electron cloud near a surface a solid. LSPs are also commonly called electromagnetic surface shape resonances, particle plasmons, and gap plasmons. The frequency or frequencies at which LSPs may be excited in a plurality of nanofeatures (e.g., nanoparticles or nanoholes) is a function of the size and shape of the nanofeature to which the surface plasmon is confined, the dielectric constant of the nanofeatures, and spacing of the nanofeatures. A plurality of nanofeatures, such as the nanoparticles 106, typically exhibits a spectrum of LSP modes that may be strongly influenced by the lattice parameter d, in addition to the size and shape of individual nanoparticles 106. Thus, the frequency or frequencies at which EMR may excite an LSP mode in each of the nanoparticles 106 may be tuned by controlling the size, shape, and spacing of the nanoparticles 106.

The substrate 102 and surface 104 thereof are formed from a material, such as a metal, alloy, or degenerately-doped semiconductor material capable of having SPPs excited therein. For example, substrate 102 may be formed from copper, gold, palladium, silver, alloys of any of the preceding metals, or another suitable material. However, in other embodiments of the present invention, the substrate 102 may be include a base formed from, for example, a glass substrate, and a thin film formed from any of the aforementioned plasmon-active materials deposited on the base.

An SPP is an electromagnetic excitation with an electromagnetic field that propagates along an interface between a material with a negative dielectric constant, such as a metal, and a medium having a real, positive dielectric constant. An SPP is generated as a result of coupling a photon to a surface plasmon of the material with the negative dielectric constant. Accordingly, the surface 104 exhibits a real, negative dielectric constant over at least a range of EMR frequencies and the medium (e.g., air) adjacent to the surface 104 exhibits a real, positive dielectric constant over at least a portion of the range of EMR frequencies that the surface 104 exhibits the real, positive dielectric constant. The surface 104 is capable of supporting an SPP mode that propagates along the surface 104. Because the SPP mode is confined to the surface 104 and regions immediately adjacent thereto, the intensity of the electric field of the SPP mode is enhanced relative to the EMR used to excite the SPP mode. The frequency of the SPP mode may be controlled, predominately, by selection of the dielectric constant of the surface 104 and the adjacent medium. The SPP mode may propagate, for example, a length of about 1 μm to about 200 μm.

Due to the dispersion relationships of free-space light and an SPP mode, the SPP mode cannot directly be excited using free-space light. In order to excite the SPP mode in the surface 104, the energy and momentum of the free-space light needs to match the energy and momentum of the SPP mode. Therefore, the diffraction grating 108 of the electric-field-enhancement structure 100, defined by the plurality of nanoparticles 106, is configured to couple EMR 110, having an excitation frequency $\omega$ and an excitation wavelength $\lambda$, emitted by an excitation source 112 to an SPP mode 114 (i.e., a planar mode) that propagates along the surface 104. The SPP mode 114 has an SPP frequency $\omega_{SPP}$ that is approximately equal to the excitation frequency $\omega$. The wavelength $\lambda$ is approximately an integer multiple of the lattice parameter d of the diffraction grating 108 (i.e., n·$\lambda$, where n is an integer and $\lambda$ is the wavelength of the EMR 110. Additionally, each of the nanoparticles 106 is also configured, by controlling the size, shape, and composition, so that each of the nanoparticles 106 exhibits an LSP mode 116 having an LSP frequency $\omega_{LSP}$ that is approximately equal to the excitation frequency $\omega$ and may be excited using the EMR 110 at the excitation frequency $\omega$.

During use, the EMR 110 having the excitation frequency $\omega$ irradiates the electric-field-enhancement structure 100 to excite the LSP modes 116 associated with the plurality of nanoparticles 106 that has the LSP frequency $\omega_{LSP}$. As previously discussed, the LSP frequency $\omega_{LSP}$ is approximately equal to the excitation frequency $\omega$ of the EMR 110. The diffraction grating 108, defined by the nanoparticles 106, also diffracts the EMR 110 and the diffracted EMR having a wavevector that coincides with the wavevector of the SPP mode 114. Therefore, the EMR 110 excites both the LSP mode 116 of each of the nanoparticles 106 and the SPP mode 114. Because the LSP modes 116 and the SPP 114 are in phase, the LSP modes 116 and the SPP 114 constructively interfere with each other to generate an electromagnetic wave having an enhanced electric field that is greater than either the enhanced electric field due to the LSP mode 116 or the SPP mode 114, individually. Additionally, the enhanced electric field may be distributed over, predominately, the entire area of the surface 104 of the substrate 102.

Figure 2:
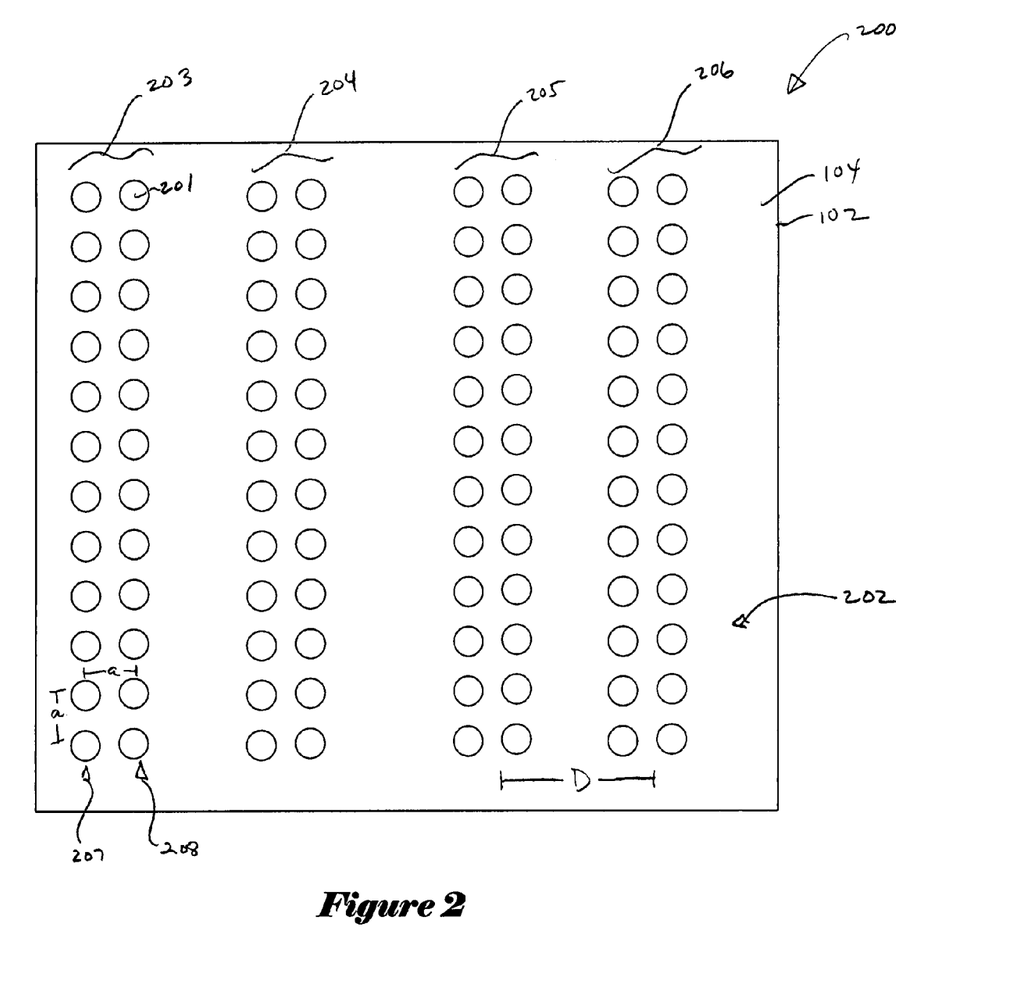
FIG. 2 is a schematic plan view of an electric-field-enhancement structure according to another embodiment of the present invention.

The design of the diffraction grating 108 shown in FIGS. 1A-1C represents merely one embodiment of the present invention. In other embodiments of the present invention, a plurality of diffraction components may be provided, each of which includes multiple nanoparticles. For example, FIG. 2 shows an electric-field-enhancement structure 200 according to one embodiment of the present invention. The electric-field-enhancement structure 200 includes a plurality of nanoparticles 201 distributed on the surface 104 of the substrate 102 to form a diffraction grating 202. The nanoparticles 201 may be formed from the same materials as the nanoparticles 106 shown in FIGS. 1A-1C. The diffraction grating 202 includes a plurality of grating components 203-206 periodically spaced from each other a distance D. Each of the grating components 203-206 may include multiple nanoparticles 201 spaced apart from each other a distance a. For example, the grating component 203 includes a row 207 and a row 208 of the nanoparticles 201. The distance D may be about 0.1 μm or more and the interparticle spacing distance α may be about 1 nm to about 10 nm. The diffraction grating 202 functions to diffract incident EMR and couple a portion of the diffracted EMR to an SPP mode associated with the surface 104, as previously described.

Figure 3A:
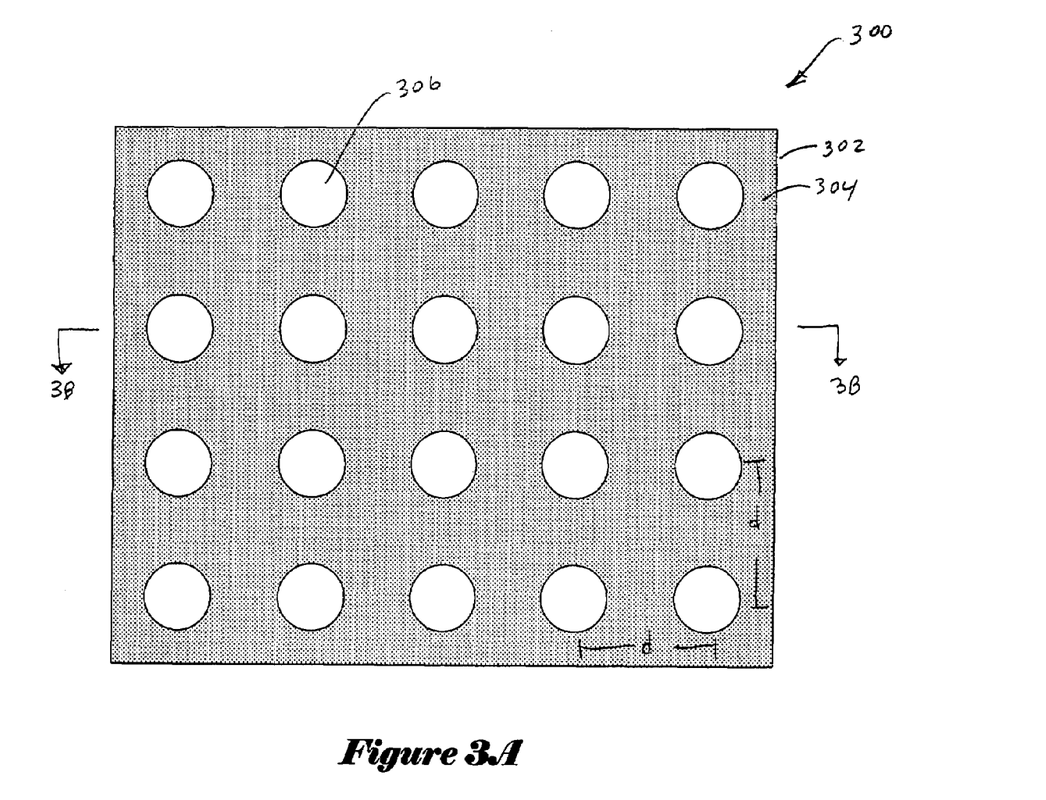
FIG. 3A is a schematic plan view of an electric-field-enhancement structure utilizing a periodic arrangement of nanoholes according to yet another embodiment of the present invention.
Figure 3B:
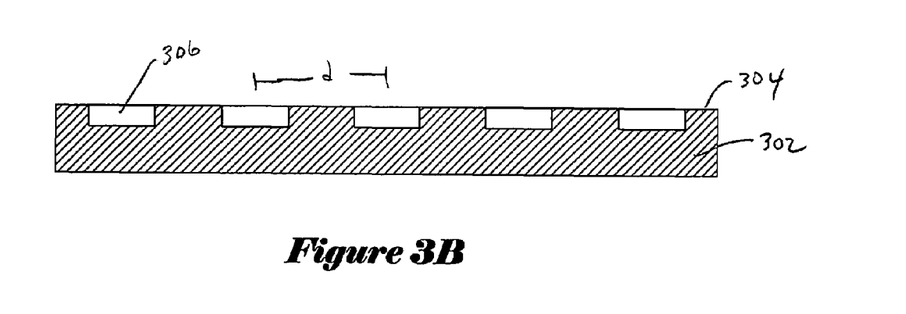
FIG. 3B is a schematic cross-sectional view of the electric-field-enhancement structure shown in FIG. 3A taken along line 3B-3B.

As alluded to above, nanoholes may be used instead of or in combination with the nanoparticles 106 or 201 shown in FIGS. 1A-1C and FIG. 2. For example, FIGS. 3A and 3B show an electric-field-enhancement structure 300 according to another embodiment of the present invention. The electric-field-enhancement structure 300 includes a substrate 302 that may be formed from the same plasmon-active materials used for the substrate 102 shown in FIGS. 1A-1C. The substrate 302 includes a surface 304 having a periodic arrangement of nanoholes 306 that may extend from the surface 304 to an intermediate depth within the substrate 302 (i.e., a blind hole) or completely through a thickness of the substrate 302 (i.e., a through hole). The nanoholes 306 are shown arranged in a square-lattice arrangement with a lattice parameter d. However, the arrangement of nanoholes 306 may exhibit other periodic arrangements, without limitation. During use, EMR may excite both LSP modes determined by the configuration and spacing of the nanoholes 306 and an SPP mode associated with the surface 304 to produce an enhanced electric field in a manner similar to the electric-field-enhancement structure 100 shown in FIGS. 1A-1C.

Figure 4:
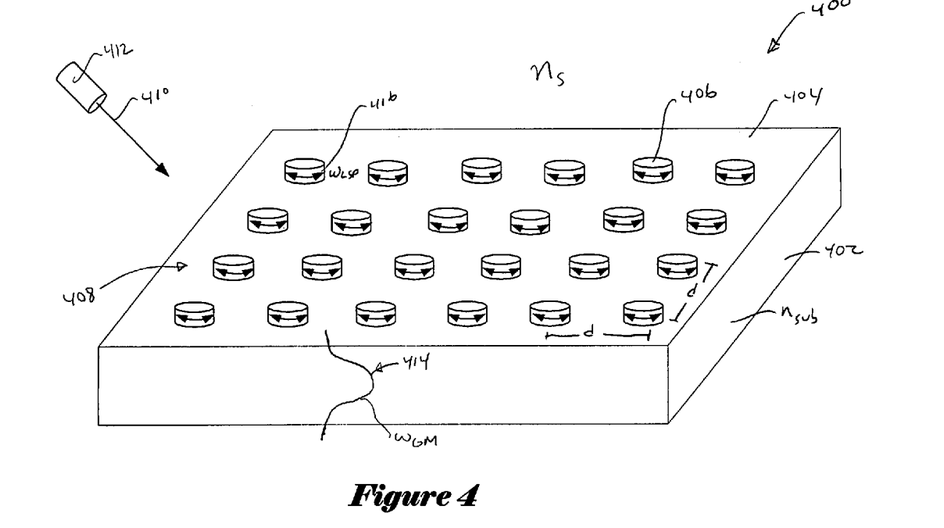
FIG. 4 is a schematic isometric view of an electric-field-enhancement structure in which the substrate comprises a dielectric material according to another embodiment of the present invention.

The electric-field-enhancement structures 100, 200, and 300 employ an SPP mode in combination with LSP modes to generate an enhanced electric field. In other embodiments of the present invention, a guided mode may be excited in a substrate in combination with LSP modes excited in a plurality of nanofeatures to generate an enhanced electric field. FIG. 4 shows an electric-field-enhancement structure 400, according to one embodiment of the present invention, which utilizes such concepts. The electric-field-enhancement structure 400 includes a dielectric substrate 402 having a surface 404. The dielectric substrate 402 may be formed from a number of different dielectric materials, such as semiconductor materials and insulating materials (e.g., silicon, silicon dioxide, etc.). A plurality of nanoparticles 406 are distributed in a periodic arrangement on the surface 404 to form a grating 408. The nanoparticles 406 may be formed from the same materials as the nanoparticles 106 shown in FIGS. 1A-1C. For example, the nanoparticles 406 are shown arranged in a square-lattice arrangement with a lattice parameter d. However, the plurality of nanoparticles 406 may exhibit other periodic arrangements, without limitation. The medium adjacent to the surface 404 exhibits a refractive index, $n_s$, that is less than that of the refractive index, $n_{sub}$, of the substrate 402.

The difference between the refractive index, $n_{sub}$, of the substrate 402 and the refractive index, $n_s$, of the medium adjacent to the surface 404 enables the substrate 402 to support a guided mode 414 (i.e., a planar mode) having a mode frequency $\omega_{GM}$. The intensity distribution of the guided mode 414 is shown superimposed on the substrate 402. The frequency $\omega_{GM}$ of the dielectric-surface mode 114 may be controlled by proper selection of the refractive index, $n_{sub}$, of the substrate 402 and the refractive index, $n_s$, of the medium adjacent to the surface 404 of the substrate 402. As previously described with respect to the electric-field-enhancement structure 100 shown in FIGS. 1A-1C, the diffraction grating 408 may be configured to couple incident EMR 410, having an excitation frequency $\omega$, emitted from an excitation source 412 to the guided mode 414. Additionally, the size, shape, composition, and spacing of the nanoparticles 406 is selected so that each of the nanoparticles 406 exhibits an LSP mode 416 having an LSP frequency $\omega_{LSP}$ that is approximately equal to both the excitation frequency $\omega$ and the dielectric-surface mode frequency $\omega_{DSW}$. Accordingly, during use, incident EMR 410 may excite both the LSP modes 416 associated with the plurality of nanoparticles 406 and the guided mode 414, which constructively interfere with each other to generate an electromagnetic field having an enhanced electric field. The guided mode 414 extends widthwise in the substrate 402 and an intensity of the guided mode 414 decays evanescently away from the surface 404 a sufficient distance so that the guided mode 414 can interact with and constructively interfere with the LSP mode 416 to generate an enhanced electric field. Stated another way, the LSP modes 416 exhibit a relatively high-loss and high-electric-field strength and mix with the low-loss and low-electric-field-strength guided mode 414 to produce a composite resonance that retains the local high-electric-field properties of the LSP modes 416. However, the composite resonance exhibits an overall loss that is lower than the LSP modes 416, allowing the electric-field strength to reach even higher magnitudes than for the LSP modes 416 individually. Although the energy density of the guided mode 414 is generally orders of magnitude less than that of an SPP mode, the propagation length may be about 1 mm to about 10 mm.

Figure 5:
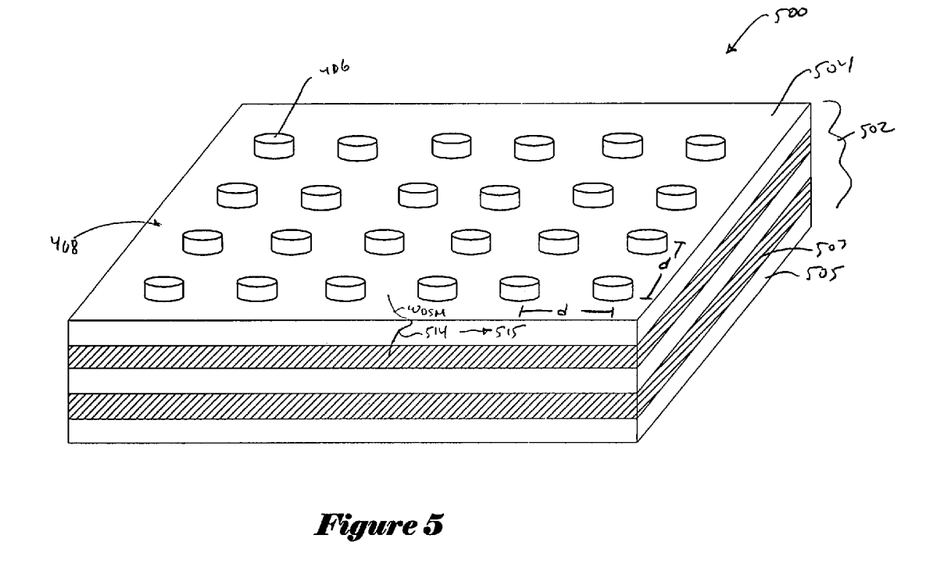
FIG. 5 is a schematic isometric view of an electric-field-enhancement structure in which the substrate is configured to support a dielectric-surface mode according to yet another embodiment of the present invention.

FIG. 5 shows an electric-field-enhancement structure 500 according to another embodiment of the present invention. The electric-field-enhancement structure 500 includes a substrate 502 having a surface 504 on which the plurality of nanoparticles 406 may be formed. The substrate 502 comprises a periodic stack of alternating dielectric layers 503 and 505. The dielectric layer 503 is a dielectric material having a first refractive index, $n_1$, and the dielectric layer 505 is a dielectric material having a second refractive index, $n_2$, that is not equal to $n_1$. Instead of supporting a guided mode within the substrate 502, the surface 504 is capable of supporting a dielectric-surface mode 514 (i.e., a planar mode) that propagates in a direction 515 and extends in a widthwise direction of the substrate 502. The intensity distribution of the dielectric-surface mode 514 is shown superimposed on the substrate 502. As shown, an intensity of the dielectric-surface mode 514 decays evanescently in a direction away from the surface 504. The dispersion relationship for the dielectric-surface mode 514 may be controlled by selection of the first refractive index $n_1$, second refractive index $n_2$, and the number of alternating layers. Thus, a mode frequency $\omega_{DSM}$ for the dielectric-surface wave 514 may be tuned by varying the above parameters (e.g., $n_1$, $n_2$, and the number of alternating dielectric layers 503 and 504) so that the mode frequency $\omega_{DSM}$ is approximately equal to the LSP frequency $\omega_{LSP}$ of each of the nanoparticles 406. Although the energy density of the dielectric-surface mode 514 is generally orders of magnitude less than that of an SPP mode, the propagation length may be about 1 mm to about 10 mm.

The plurality of nanoparticles 106, 201, and 406 may be formed from a number of well-known fabrication techniques. For example, nanoparticles may be formed by depositing a thin film made from a plasmon-active material onto a substrate and annealing the thin film at a sufficient temperature and for a sufficient time to cause agglomeration of the plasmon-active material. If desired, such as in the diffraction grating 202 shown in FIG. 2, a portion of the nanoparticles so formed may be removed using a lithographic technique (e.g., electron-beam lithography or photolithography) or focused ion beam milling. For larger nanoparticle or nanohole sizes, nanoparticles or nanoholes may be directly defined in a thin film or substrate formed from a plasmon-active material using nanoimprint lithography, electron-beam lithography, focused ion beam milling, or another suitable technique.

Figure 6:
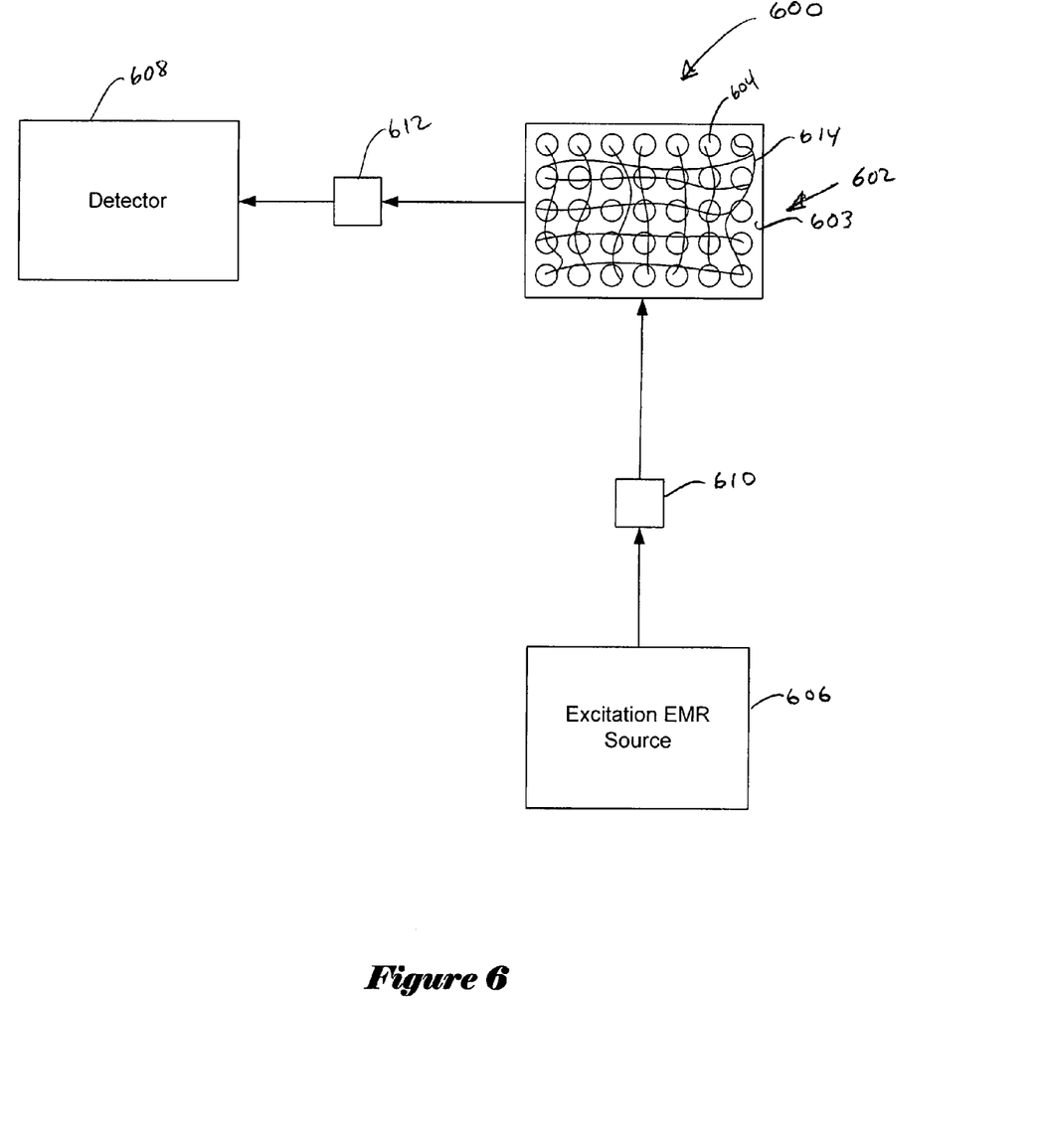
FIG. 6 is a functional block diagram of a detection apparatus that may use any of the disclosed electric-field-enhancement structures according to one embodiment of the present invention.

Any of the aforementioned embodiments of electric-field-enhancement structures shown and described with respect to FIGS. 1A-5 may be used in a number of different detection apparatuses. For example, the, disclosed electric-field-enhancement structures may be utilized in detection apparatuses for use as sensors and analytical instruments (e.g., a lab-on-chip or a larger desktop analytical instrument). FIG. 6 shows a functional block diagram of a detection apparatus 600 according to one embodiment of the present invention. The detection apparatus 600 may be operated as a Raman or infrared spectroscopy system. The detection apparatus 600 includes an electric-field-enhancement structure 602 that may be configured as any of the previously described electric-field-enhancement structures 100, 200, 300, 400, and 500. However, for illustrative purposes, the electric-field-enhancement structure 600 is depicted with a substrate 603 supporting a plurality of nanofeatures 604 represented as nanoparticles. In certain embodiments of the present invention, the nanoparticles and/or the substrate 603 may be coated with functionalized molecules to promote bonding of specific analytes to the nanoparticles and/or the substrate 603. The detection apparatus 600 further includes an excitation EMR source 606 and a detector 608. The detection apparatus 600 may also include various optical components 610 positioned between the excitation EMR source 606 and the electric-field-enhancement structure 602, and various optical components 612 positioned between the electric-field-enhancement structure 602 and the detector 608.

The excitation EMR source 606 may include any suitable source for emitting EMR at a desired wavelength/frequency, and may be capable of emitting a tunable wavelength/frequency of EMR. For example, commercially available semiconductor lasers, helium-neon lasers, carbon dioxide lasers, light emitting diodes, incandescent lamps, and many other known EMR-emitting sources may be used as the excitation EMR source 606. The EMR emitted by the excitation EMR source 606 may be any suitable wavelength/frequency for analyzing an analyte using Raman or infrared spectroscopy and exciting LSP modes of the plurality of nanofeatures 604 and a planar mode of the substrate 603. For example, the planar mode may be an SPP mode, a guided mode, or a dielectric-surface mode depending on the configuration of the substrate 603. For example, the excitation EMR source 606 may emit EMR having a range of wavelengths from about 350 nm to about 1000 nm. The excitation EMR emitted by the excitation EMR source 606 may be delivered directly from the EMR source 606 to the electric-field-enhancement structure 602. Alternatively, collimation, filtration, and subsequent focusing of the excitation radiation may be performed by optical components 610 before the excitation EMR impinges on the electric-field-enhancement structure 602. The optical components 610 may further include one or more polarizing plates for selectively controlling a polarization direction of the excitation EMR.

When the detection apparatus 600 is employed as a Raman spectroscopy system, the electric-field-enhancement structure 602 may enhance the Raman signal of the analyte. In other words, irradiation of the plurality of nanofeatures 604 and the substrate 603 simultaneously excites LSP modes of the plurality of nanofeatures 604 and a planar mode of the substrate 603 that constructively interfere with each to generate an enhanced electric field, as previously described. The enhanced electric field may increase the number photons inelastically scattered by an analyte 614 positioned near or adjacent to the plurality of nanofeatures 604 and the substrate 603.

The Raman scattered photons may be collimated, filtered, or focused with optical components 612. For example, a filter or a plurality of filters may be employed, either as part of the structure of the detector 608, or as a separate unit that is configured to filter the wavelength of the excitation radiation, thus allowing only the Raman scattered photons to be received by the detector 608. The detector 608 receives and detects the Raman scattered photons and may include a monochromator (or any other suitable device for determining the wavelength of the Raman scattered photons) and a device such as, for example, a photomultiplier for determining the quantity of Raman scattered photons (intensity).

To perform Raman spectroscopy using the detection apparatus 600, a user may provide an analyte 614 adjacent to the plurality of nanofeatures 604 of the electric-field-enhancement structure 602. The analyte 614 and the electric-field-enhancement structure 602 are irradiated with excitation EMR from the excitation EMR source 606. For Raman spectroscopy, the wavelength of the excitation EMR is typically in the ultraviolet wavelength range. Then, Raman scattered photons scattered by the analyte are detected by the detector 608. The enhanced electric field generated by the electric-field-enhancement structure 602 responsive to the excitation EMR may increase the intensity of the Raman scattered photons by a factor of about $10^8$ to about $10^{16}$ that is capable of detecting single molecules or other very low concentrations of analyte.

The detection apparatus 600 may also be operated as a reflection-absorption infrared spectroscopy ("RAIRS") system. In such an embodiment, the electric-field-enhancement structure 602 is designed to generate an enhanced electric field responsive to EMR from the EMR source 600 at a specific frequency. The specific frequency of excitation EMR emitted from the EMR source 600 may also generally correspond to a vibration mode of the analyte 614. During use, infrared EMR may be emitted from the excitation EMR source 600 over a wide or narrow range of frequencies that includes the specific frequency corresponding to the vibrational mode of the analyte 612. The incident infrared EMR irradiates the analyte 614 and the electric-field-enhancement structure 602. For infrared EMR at the specific frequency, an enhanced electric field is generated by the electric-field-enhancement structure 602, as previously described. The enhanced electric field promotes absorption of the IR EMR by the analyte 614 at the vibrational mode of the analyte 614. The detector 608 detects infrared EMR reflected from the electric-field-enhancement structure 602, and a pronounced dip in the reflection spectrum may be observed at the vibrational mode of the analyte 614 indicating the presence of a specific type of molecule. The enhanced electric field generated by the electric-field-enhancement structure 602 may increase the absorption of infrared EMR by the analyte 614 at or near the specific frequency by a factor of about $10^8$ to about $10^{16}$. With such enhanced absorption, the detection apparatus 600 may be capable of detecting single molecules or other very low concentrations of analyte.

Figure 7:
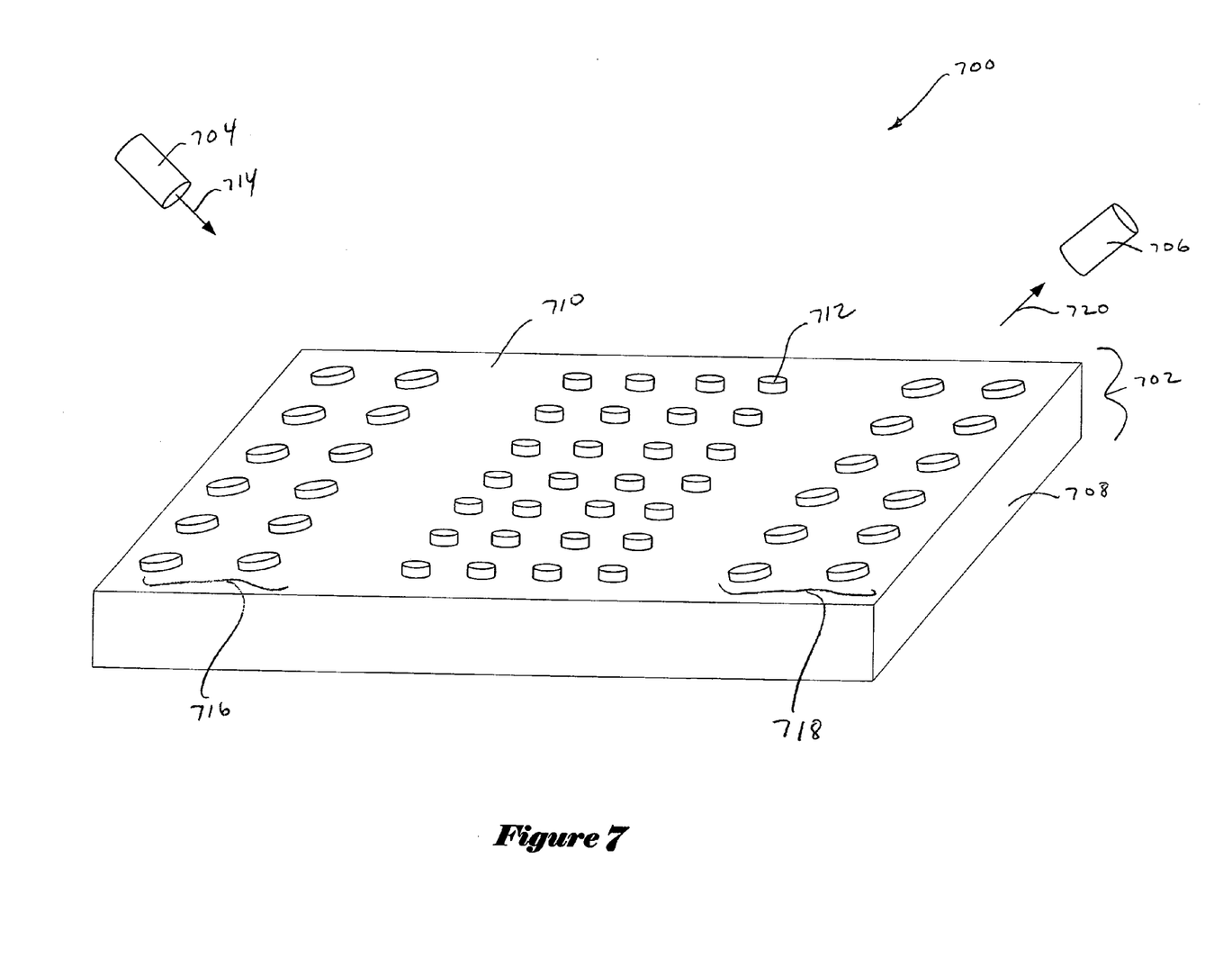
FIG. 7 is a schematic isometric view of a detection apparatus including an electric-field-enhancement structure utilizing multiple diffraction gratings according to one embodiment of the present invention.

FIG. 7 show a detection apparatus 700 according to another embodiment of the present invention. The detection apparatus 700 includes an electric-field-enhancement structure 702, an excitation EMR source 704, and a detector 706. The electric-field-enhancement structure 702 includes a substrate 708 having a surface 710 on which a plurality of nanofeatures 712 is formed. For example, in the illustrated embodiment, each of the nanofeatures 712 is a nanoparticle made from a plasmon-active material. However, all or some of the nanofeatures 712 may be nanoholes formed in the surface 710 of the substrate 708. As with the previously described electric-field-enhancement structures, the plurality of nanofeatures 712 and the substrate 708 are designed so that LSP modes of each of the nanofeatures 712 and a planar mode (e.g., an SPP mode, a dielectric-surface mode, or a guided mode) of the substrate 708 are excited substantially simultaneously by EMR 714 at a frequency ω emitted by the excitation EMR source 704. In certain embodiments of the present invention, the nanoparticles and/or the surface 710 of the substrate 708 may be coated with functionalized molecules to promote bonding of specific analytes to the nanoparticles and/or the surface 710.

The electric-field-enhancement structure 702 further includes a first diffraction grating 716 that may be positioned on one side of the plurality of nanofeatures 712 and configured to diffract the EMR 714 at the frequency ω to the planar mode supported by the substrate 708. A second diffraction grating 718 may be positioned on an opposing side of the plurality of nanofeatures 712 and configured to diffract EMR coupled to the planar mode of the substrate 708. According to various embodiments of the present invention, the first and second diffraction gratings 716 and 718 may be configured to diffract different frequencies of EMR or the same frequency of EMR. The first and second diffraction grating 716 and 718 may be formed from an array of suitable sized and configured particles or holes (e.g., nanoparticles and/or nanoholes).

In certain embodiments of the present invention, the excitation EMR source 704 may be a laser diode (e.g., a vertical cavity or edge emitting laser diode) formed on or mounted to the substrate 708 adjacent to the first diffraction grating 716. In such an embodiment, the detector 706 may be a photodiode (e.g., a PIN photodiode) that is also formed on or mounted to the substrate 708 adjacent to the second diffraction grating 718.

In one embodiment of the present invention, the detection apparatus 700 may be operated as a Raman spectroscopy system. In such an embodiment, the excitation EMR source 704 emits the EMR 714 at the frequency ω. The EMR 714 is diffracted from the first diffraction grating 716 as a beam that irradiates an analyte (not shown) situated on or near the plurality of nanofeatures 712, and excites the LSP modes of each of the nanofeatures 712 and the planar mode of the substrate 708 to generate an enhanced electric field. As previously described with respect to the detection apparatus 600, the enhanced electric field increases the amount of Raman EMR scattered from the analyte and at least a portion of the Raman EMR is coupled to the planar mode of the substrate 708. Although the frequency of the inelastically scattered Raman EMR is either slightly greater (anti-Stokes radiation) or slightly less (Stokes radiation) than that of the frequency ω of the EMR 714, the frequency spread of the Stokes radiation, anti-Stokes radiation, or both generally falls within the frequency spread of the planar mode. The second diffraction grating 718 may be configured to preferentially diffract the Raman EMR coupled to the planar mode shown as diffracted beam 720, which may be received by the detector 706. The Raman EMR is characteristic of the chemical composition of the analyte being analyzed. The signal-to-noise ratio can be improved because the second diffraction grating 718 may be configured to be highly selective to diffract only the Stokes or anti-Stokes Raman EMR coupled to the planar mode.

In another embodiment of the present invention, the detection apparatus 700 may be operated as an infrared spectroscopy system. In such an embodiment, the excitation EMR source 704 emits the EMR 714 at the frequency ω that falls within the infrared frequency range. The EMR 714 is diffracted from the first diffraction grating 716 as a beam that irradiates an analyte (not shown) situated on the plurality of nanofeatures 712, and excites the LSP modes of each of the nanofeatures 712 and the planar mode of the substrate 708 to generate an enhanced electric field. However, when the analyte is present, a portion of the diffracted beam is absorbed by the analyte and a portion of the diffracted beam is coupled to the planar mode of the substrate 708. The second diffraction grating 718 may be configured to diffract the EMR at the frequency ω coupled to the planar mode shown as diffracted beam 720, which may be detected by the detector 706. Thus, when operated as an infrared spectroscopy system, the second diffraction grating 718 is configured to diffract generally the same frequency of EMR as the first diffraction grating 716. The intensity of the diffracted beam 720 is less intense when the analyte is present because a certain portion of the beam diffracted from the first diffraction grating 716 is absorbed by the analyte (not shown). Thus, a drop in the intensity of the diffracted beam 720 compared to when the analyte is not present is indicative of the presence of a certain type of analyte.

Figure 8:
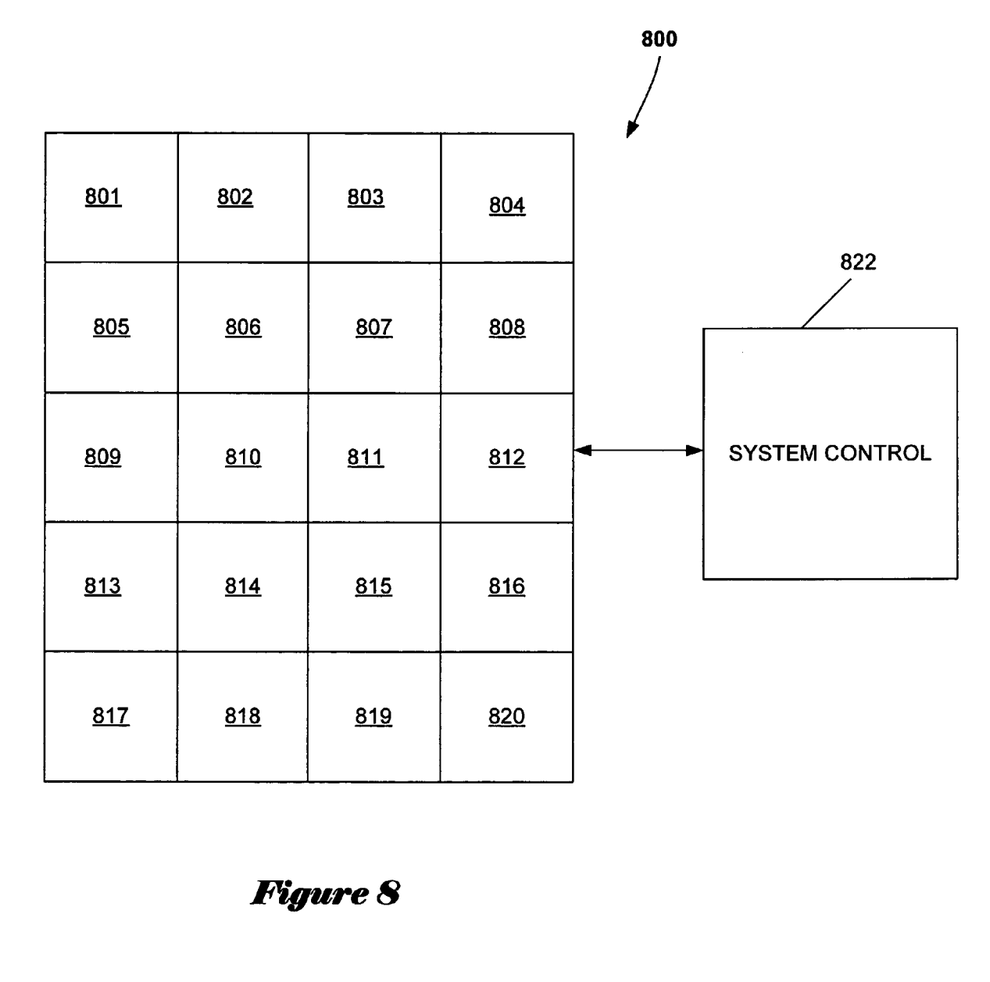
FIG. 8 is a functional block diagram of a detection apparatus that includes a plurality of detection apparatus sub-units configured as any of the disclosed detection apparatuses according to one embodiment of the present invention.

FIG. 8 shows a detection apparatus 800 according to yet another embodiment of the present invention. The detection apparatus 800 includes a plurality of detection apparatus sub-units 801-820, each of which may be configured as any of the previously described detection apparatus embodiments. The detection apparatus sub-units 801-820 may be formed on a common substrate or each of the detection apparatus sub-units 801-820 may be discrete units that are assembled together. Each of the detection apparatus sub-units 801-820 may include an electric-field-enhancement structure configured to enhance an incident electric field of a different, selected frequency. Thus, each of the detection apparatus sub-units 801-820 may be used to detect a specific type of analyte. The detection apparatus 800 further includes a system control 822 operable to control the detection apparatus sub-units 801-820 and receive data generated by the detection apparatus sub-units 801-820. The system control 822 may further includes a suitable user interface (not shown) to display the data generated from the detection apparatus sub-units 801-820 and further process and/or manipulate the data. In certain embodiments of the present invention, the detection apparatus 800 a portion of the detection apparatus sub-units 801-820 may be configured to perform Raman spectroscopy and a portion of the detection apparatus sub-units 801-820 may be configured to perform infrared spectroscopy.

Although not illustrated, microfluid channels may be formed on or within the substrates of the electric-field-enhancement structures of the disclosed detection apparatuses. Moreover, other well-known microfluid components may be provided. For example, micropumps may be used to pump analyte onto or near a plurality of nanofeatures of the electric-field-enhancement structures for analysis and/or detection.

The foregoing description, for purposes of explanation, used specific nomenclature to provide a thorough understanding of the present invention. However, it will be apparent to one skilled in the art that the specific details are not required in order to practice the present invention. The foregoing descriptions of specific embodiments of the present invention are presented for purposes of illustration and description. They are not intended to be exhaustive of or to limit the present invention to the precise forms disclosed. Many modifications and variations are possible in view of the above teachings. The embodiments are shown and described in order to best explain the principles of the present invention and its practical applications, to thereby enable others skilled in the art to best utilize the present invention and various embodiments with various modifications as are suited to the particular use contemplated. It is intended that the scope of the present invention be defined by the claims and their equivalents:

The invention claimed is:

1. An electric-field-enhancement structure, comprising:
a substrate including a surface, the substrate capable of supporting a planar mode having a planar-mode frequency; and
a plurality of nanofeatures formed on or in the surface of the substrate, each of the nanofeatures exhibiting a localized-surface-plasmon ("LSP") mode having a LSP frequency approximately equal to the planar-mode frequency, wherein the LSP mode of each of the nanoparticles and the planar mode constructively interfere with each other when excited.

2. The electric-field-enhancement structure of claim 1 wherein the plurality of nanofeatures comprises at least one of:
nanoholes formed in the surface of the substrate; and
nanoparticles distributed over the surface of the substrate.

3. The electric-field-enhancement structure of claim 1 wherein:
the surface of the substrate comprises a metallic material, with the surface positioned adjacent to a dielectric medium; and
the planar mode comprises a surface-plasmon-polariton mode.

4. The electric-field-enhancement structure of claim 1 wherein:
the substrate comprises one or more dielectric layers; and
the planar mode comprises a dielectric-surface mode or a guided mode.

5. The electric-field-enhancement structure of claim 1 wherein the plurality of nanofeatures defines a diffraction grating configured to couple electromagnetic radiation incident thereon to the planar mode.

6. The electric-field-enhancement structure of claim 5 wherein the diffraction grating comprises a plurality of grating components each of which includes more than one nanofeature of the plurality of nanofeatures.

7. The electric-field-enhancement structure of claim 1, further comprising:
a first diffraction grating comprising particles formed on or holes formed in the substrate and configured to couple excitation electromagnetic radiation incident thereon to the planar mode; and
a second diffraction grating comprising particles formed on or holes formed in the substrate, the second diffraction grating spaced from the first diffraction grating with the plurality of nanofeatures positioned between the first and the second diffraction gratings, wherein the second diffraction grating configured to diffract electromagnetic radiation having a frequency different than that of the excitation electromagnetic radiation.

8. The electric-field-enhancement structure of claim 1, further comprising:
a first diffraction grating comprising particles formed on or holes formed in the substrate and configured to couple excitation electromagnetic radiation incident thereon to the planar mode; and
a second diffraction grating comprising particles formed on or holes formed in the substrate, the second diffraction grating spaced from the first diffraction grating with the plurality of nanofeatures positioned between the first and the second diffraction gratings, wherein the second diffraction grating configured to diffract the excitation electromagnetic radiation coupled to the planar mode.

9. A detection apparatus, comprising:
at least one excitation source operable to emit excitation electromagnetic radiation at a first frequency;
a first electric-field-enhancement structure including:
a first substrate including a first surface, the first substrate capable of supporting a first planar mode having a first planar-mode frequency;
a first plurality of nanofeatures formed on or in the first surface, each of the nanofeatures of the first plurality of nanofeatures exhibiting a first localized-surface-plasmon ("LSP") mode having a first LSP frequency approximately equal to the first planar-mode frequency, wherein the first LSP mode of each of the first plurality of nanofeatures and the first planar mode are excited responsive to the excitation radiation at the first frequency; and
at least one detector operably coupled to the first electric-field-enhancement structure.

10. The detection apparatus of claim 9 wherein the first plurality of nanofeatures comprises at least one of:
nanoholes formed in the surface of the substrate; and
nanoparticles distributed over the surface of the substrate.

11. The detection apparatus of claim 9 wherein the first planar mode comprises one of:
a surface-plasmon-polariton mode;
a guided mode; and
a dielectric-surface mode.

12. The detection apparatus of claim 9 wherein the first plurality of nanofeatures defines a diffraction grating configured to couple the excitation electromagnetic radiation incident thereon to the first planar mode.

13. The detection apparatus of claim 9, further comprising:
a first diffraction grating comprising particles formed on or holes formed in the substrate and configured to couple excitation electromagnetic radiation incident thereon to the planar mode; and
a second diffraction grating comprising particles formed on or holes formed in the substrate, the second diffraction grating spaced from the first diffraction grating with the plurality of nanofeatures positioned between the first and the second diffraction gratings, wherein the second diffraction grating configured to diffract Raman electromagnetic radiation coupled to the first planar mode from an analyte positioned adjacent to the nanofeatures.

14. The detection apparatus of claim 9, further comprising:
a first diffraction grating comprising particles formed on or holes formed in the substrate and configured to couple excitation electromagnetic radiation incident thereon to the planar mode; and
a second diffraction grating comprising particles formed on or holes formed in the substrate, the second diffraction grating spaced from the first diffraction grating with the plurality of nanofeatures positioned between the first and the second diffraction gratings, wherein the second diffraction grating configured to diffract a portion of the excitation electromagnetic radiation unabsorbed by an analyte positioned adjacent to the nanofeatures and coupled to the first planar mode.

15. The detection apparatus of claim 9:
wherein the at least one excitation source is further operable to emit excitation electromagnetic radiation at a second frequency; and
further comprising:
at least a second electric field-enhancement structure including:
a second substrate including a second surface, the second substrate capable of supporting a second planar mode having a second planar-mode frequency; and a second plurality of nanofeatures associated with the second surface, each of nanofeatures of the second plurality of nanofeatures exhibiting a second LSP mode having a second LSP frequency approximately equal to the second planar-mode frequency, wherein the second LSP mode of each of the second plurality of nanofeatures and the second planar mode are excited responsive to the electromagnetic radiation at the second frequency.

16. A method of generating an enhanced electric field, the method comprising:

irradiating a plurality of nanofeatures formed on or in a surface of a substrate using excitation electromagnetic radiation;

responsive to irradiation of the plurality of nanofeatures, exciting a localized-surface-plasmon ("LSP") mode in each of the nanofeatures;

responsive to irradiation of the plurality of nanofeatures, exciting a planar mode in the surface of the substrate; and constructively interfering the LSP mode excited in each of the nanofeatures and the planar mode excited in the surface to produce the enhanced electric field.

17. The method of claim 16 wherein irradiating a plurality of nanofeatures comprises at least one:

irradiating a plurality of nanoparticles distributed over the surface of the substrate; and irradiating a plurality of nanoholes formed in the surface of the substrate.

18. The method of claim 16 wherein irradiating a plurality of nanofeatures comprises:

coupling the electromagnetic radiation to the planar mode by diffracting the electromagnetic radiation using the nanofeatures.

19. The method of claim 16, further comprising:

disposing an analyte adjacent to the plurality of nanofeatures; and detecting a portion of the excitation electromagnetic radiation unabsorbed by the analyte and coupled to the planar mode of the surface.

20. The method of claim 16, further comprising:

disposing an analyte adjacent to the plurality of nanofeatures; and detecting Raman electromagnetic radiation emitted by the analyte responsive to the excitation electromagnetic radiation and coupled to planar mode.

* * * * *